(12) United States Patent
Nakajima

(10) Patent No.: US 6,183,439 B1
(45) Date of Patent: Feb. 6, 2001

(54) DEVICE FOR WINDING AND STORING A USED NEEDLE OF AN INJECTOR

(75) Inventor: Noboru Nakajima, Tokyo (JP)

(73) Assignee: Medikit Co., Ltd, Tokyo (JP)

( * ) Notice: Under 35 U.S.C. 154(b), the term of this patent shall be extended for 0 days.

(21) Appl. No.: 09/127,036

(22) Filed: Jul. 31, 1998

(30) Foreign Application Priority Data

Mar. 20, 1998 (JP) ................................................. 10-071775

(51) Int. Cl.[7] .................................................. A61M 5/00
(52) U.S. Cl. ........................... 604/110; 604/192; 128/919
(58) Field of Search ..................................... 604/110, 192, 604/195, 198, 240, 243, 263, 162, 167; 128/917, 919

(56) References Cited

U.S. PATENT DOCUMENTS

| | | | |
|---|---|---|---|
| 4,266,544 | * 5/1981 | Wardlaw | 604/110 |
| 4,634,428 | * 1/1987 | Cuu | 604/192 |
| 5,019,048 | * 5/1991 | Margolin | 604/192 |
| 5,084,019 | * 1/1992 | Gartz | 604/110 |
| 5,084,020 | * 1/1992 | Gartz | 604/110 |
| 5,476,106 | * 12/1995 | Gartz | 604/110 |

FOREIGN PATENT DOCUMENTS 1-136665   5/1989   (JP) .

* cited by examiner

*Primary Examiner*—Ronald K. Stright, Jr.
(74) *Attorney, Agent, or Firm*—Arent Fox Kintner Plotkin & Kahn PLLC

(57) ABSTRACT

A device for winding and storing a used needle of an injector. The device includes a needle-hub assembly, a cylindrical container and a needle winding axle. A hub of the needle-hub assembly is arranged through a bottom wall of the cylindrical container at an eccentric position relative to a longitudinal axis thereto. After using the injector, the cylindrical container is rotated about the needle winding axle, whereby the used needle is wound and finally stored within the cylindrical container.

6 Claims, 3 Drawing Sheets

DEVICE FOR WINDING AND STORING A USED NEEDLE OF AN INJECTOR

BACKGROUND OF THE INVENTION

1. Field of the Invention

The present invention relates to an injector for medical use having a needle fixed to its syringe, particularly to a safety injector which permits the used needle to be handled with safety.

2. Description of Related Art

One example of such safety injector is disclosed in Japanese Patent 1-136665(A). This prior art injector includes adisposable container for containing the needle after used and removed from the syringe.

More specifically the used needle can be removed from the syringe by using the cover plate of the disposable container, not directly using one's fingers. For this purpose the cover plate is designed to have a slot made therein, comprising a wide section for receiving the flanged end of the needle and a narrow section for catching the flanged end of the needle. The whole length of used needle is inserted from the wide section of the slot in the disposable container, and the syringe is moved toward the narrow section of the slot so that the flange of the needle may be put in contact with the rear side of the cover plate across the narrow section of the slot. Then, the syringe is pulled up to leave the used needle in the disposable container.

Inconveniently injectors must be carried always along with associated disposable containers, and such disposable containers must be put aside when using the injectors. More disadvantageously after using the injector a doctor or nurse inserts the used needle into the slot of the disposable container. On this occasion there is a danger of injuring his or her hand or finger with the contaminated needle. If the syringe-and-needle is not moved so far as to put the needle completely in the narrow section of the slot of the cover plate, it may happen that the contaminated needle is not removed from the syringe when the syringe is pulled up from the disposable container, and then the contaminated needle is likely to injure one's hand or finger as a result of counter action to the pulling-up of the syringe.

There has been, therefore, an increasing demand for reducing such inconvenience and danger in handling injectors.

SUMMARY OF THE INVENTION

To meet such demand a safety injector having a needle-and-hub body attached thereto is improved according to the present invention in that it has needle winding-and-storing means equipped therewith, said needle winding-and-storing means comprising a cylindrical container and a needle winding axle rotatably fixed therein.

The cylindrical container has a small through hole made therein for the needle of the needle-and-hub body to pass therethrough; and the needle winding axle has the hub of the needle-and-hub body fixed thereto, permitting the cylindrical container to rotate about the needle winding axle. The cylindrical container is adapted to turn about the needle winding axle, which stands aside from the hub of the needle-and-hub body, thereby permitting the needle winding axle to pull in and wind the needle of the needle-and-hub body therearound. The injector may further comprise detent means for preventing the cylindrical container from rotating in the opposite or unwinding direction. It may further comprise rattle-proof means provided between the needle winding axle and the cylindrical container, thereby preventing the rattling or inadvertent rotation of the cylindrical container before the needle-winding operation starts.

The injector may further comprise a thumb catch integrally connected to the hub of the needle-and-hub body or the needle winding axle for assisting the needle-winding operation. The needle of the needle-and-hub body may be a thin needle, soft needle or resin needle of all or partial resin, thereby facilitating the winding of the needle of the needle-and-hub body.

The safety injector permits the pulling-in and coiling of the needle immediately after being used until the needle end disappears from the disposable container, thereby assuring that nobody may be injured by the contaminated needle. The injector whose disposable container contains a contaminated needle can be disposed of.

The disposable container is fixed to the syringe of the injector, thereby eliminating any inconvenience which otherwise, would be caused by carrying a separate disposable container along with an injector. Thanks to means for preventing rotation of the disposable container in the unwinding direction and rattle-proof means the injector can be handled with safety.

Other objects and advantages of the present invention will be understood from the following description of some safety injectors according to preferred embodiments of the present invention, which are shown in accompanying drawings.

DESCRIPTION OF THE PREFERRED EMBODIMENTS

Figure 1:
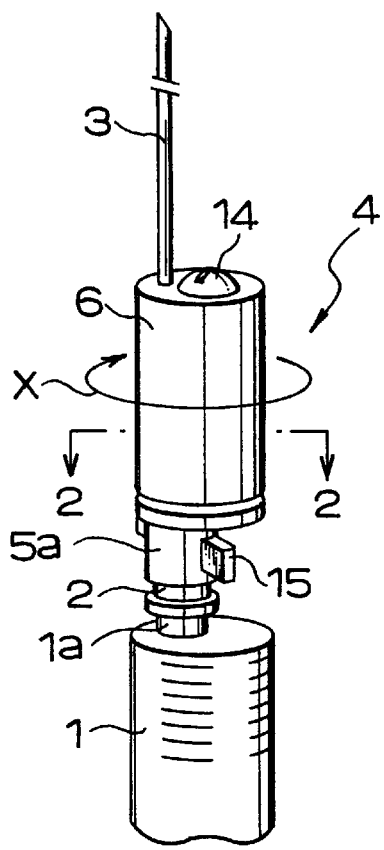
FIG. 1 is a perspective view of a safety injector according to a first embodiment of the present invention.
Figure 2:
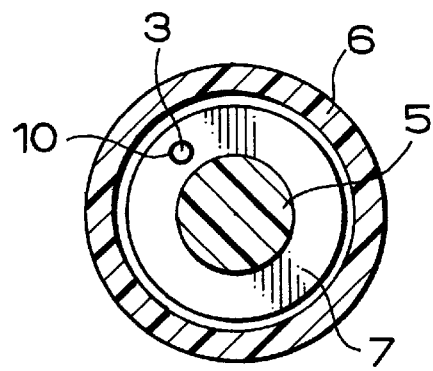
FIG. 2 is an enlarged cross-section of the safety injector taken along the line 2—2 in FIG. 1.

FIGS. 1 to 7 show a safety injector according to the first embodiment of the present invention. As shown, a safety injector has a needle-and-hub body attached to its liquid outlet-and-inlet projection 1a, and a needle winding-and-storing means 4 fixed to the hub 2 of the needle-and-hub body.

The needle winding-and-storing means 4 comprises a needle winding axle 5 fixed to the hub 2 of the needle-and-hub body, and a cylindrical container 6 rotatably fixed to the needle winding axle 5. Specifically the needle winding axle 5 has a longitudinal extension 5a integrally formed at an eccentric position to its central axis, and the longitudinal eccentric extension 5a of the needle winding axle 5 is bonded to the hub 2 of the needle-and-hub body.

Figure 3:
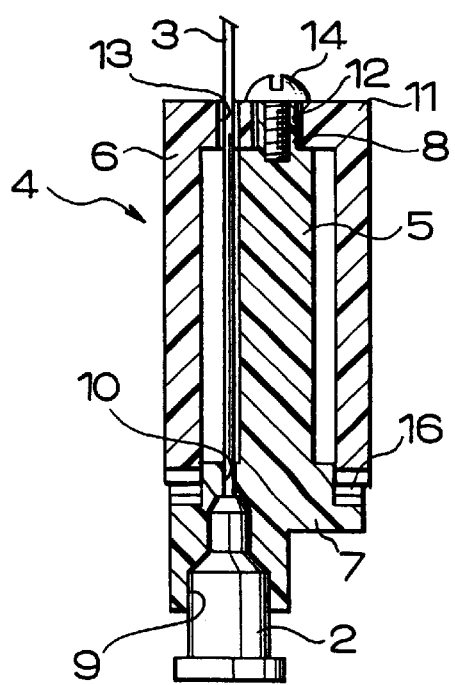
FIG. 3 is an enlarged longitudinal section of the disposable container of the safety injector.

As seen from FIG. 3, the needle winding axle 5 has a plateau-like flange 7 integrally formed to its bottom end and a center protrusion 8 integrally formed to its top end. The eccentric extension 5a is integrally formed in the plateau-like flange 7. Also, the eccentric extension 5a has a recess 9 made therein for accommodating the hub 2 of the needle-and-hub body and a small through hole 10 consecutive to the recess 9 for permitting the needle of the needle-and-hub body to pass therethrough.

The cylindrical container 6 has a large through hole 12 made at the center of the ceiling plate 11 for accommodating the center protrusion 8 of the needle winding axle 5, and a small through hole 13 made in the ceiling plate 11 for permitting the needle of the needle-and-hub body to pass therethrough.

The cylindrical container 6 is rotatably fixed to the needle winding axle 5 by putting on the needle winding axle 5 and by fixing the center protrusion 8 of the needle winding axle 5 to the ceiling plate 11 with a headed fastener 14.

The eccentric extension 5a has a thumb catch 15 integrally connected thereto for positively holding the syringe 1 and the needle winding axle 5, thereby permitting stable rotation of the cylindrical container 6 to assist the needle-winding operation.

In order to assure a stable rotation of the cylindrical container 6 in the winding direction detent means is provided for instance, between the bottom of the cylindrical container 6 and the plateau-like flange 7 of the needle winding axle 5.

Figure 4:
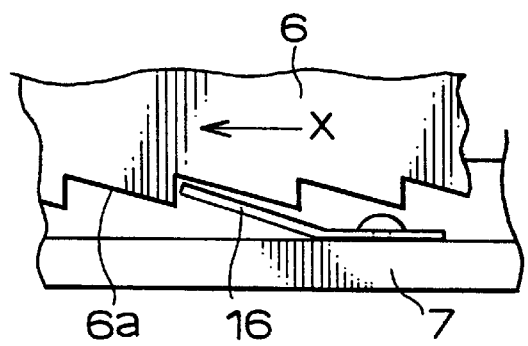
FIG. 4 is an enlarged side view of the fragment of one example of anti-unwinding means of the safety injector.

FIG. 4 shows one example of such detent means, which comprises sawtooth-like indentations 6a made on the annular bottom of the cylindrical container 6, and a resilient ramp piece 16 to detachably engage with the sawtooth-like indentations 6a. The resilient ramp piece 16 can be yieldingly bent when the cylindrical container 6 rotates in the winding direction as indicated by arrow "x", but a selected sawtooth-like indentation will be caught by the resilient ramp piece 16 when the cylindrical container 6 is going to turn in the unwinding direction. The resilient ramp piece 16 can be a spring plate, and can be fixed at least one selected position on the plateau-like flange 7.

Figure 5:
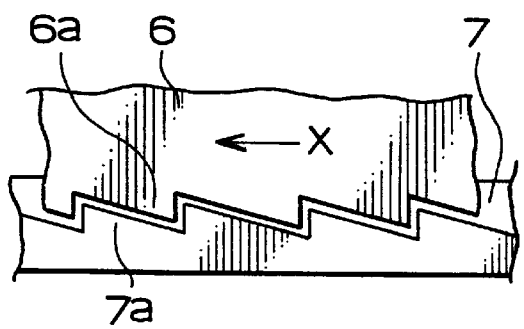
FIG. 5 is an enlarged side view of the fragment of another example of anti-unwinding means of the safety injector.

FIG. 5 shows another example of such detent means making use of the resiliency of a resin material of which the cylindrical container 6 and the needle winding axle 5 are made. It comprises sawtooth-like indentations 6a and 7a made both on the annular bottom of the cylindrical container 6 and the plateau-like flange 7, leaving a narrow gap therebetween. These sawtooth-like indentations 6a and 7a can be somewhat deformed to permit the overlying indentations 6a to ride over the underlying indentations 7a only in rotating the cylindrical container 6 in the winding direction as indicated by arrow "x".

Figure 6:
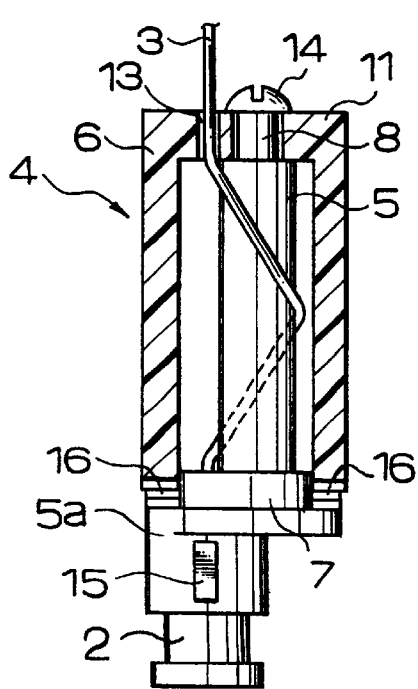
FIG. 6 is an enlarged longitudinal section of the disposable container similar to FIG. 3, illustrating that the needle is wound one turn about the needle winding axle.
Figure 7:
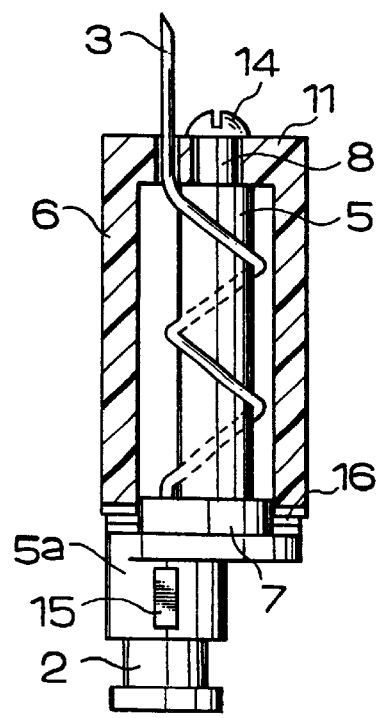
FIG. 7 is an enlarged longitudinal section of the disposable container similar to FIG. 3, illustrating that the needle is wound two turns about the needle winding axle.
Figure 8:
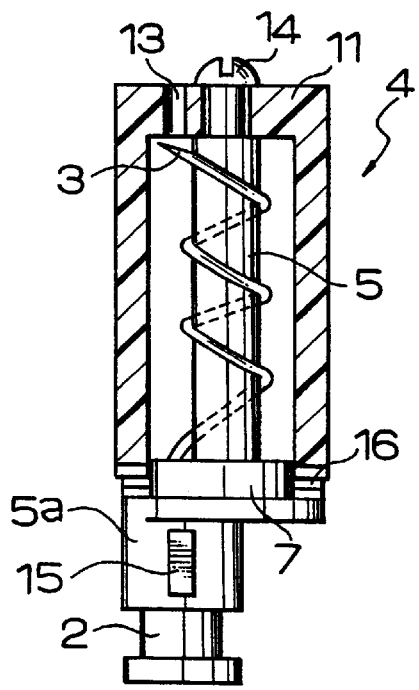
FIG. 8 is an enlarged longitudinal section of the disposable container similar to FIG. 3, illustrating that the needle is wound three turns about the needle winding axle.

FIGS. 6 to 8 illustrate the manner in which the needle winding axle 5 pulls in and wind the used needle therearound. Specifically the syringe 1 is held in the left hand with the thumb catch 15 caught by the thumb, and the cylindrical container 6 is held in the right hand to rotate the cylindrical container 6 in the winding direction as indicated by arrow "x" (FIG. 1). Thus, the cylindrical container 6 turns clockwise about the needle winding axle 5.

The hub 2 of the needle-and-hub body is fixed to the eccentric extension 5a of the plateau-like flange 7 of the needle winding axle 5, and therefore, the clockwise rotation of the cylindrical container 6 causes the used needle of the needle-and-hub body to be wound about the needle winding axle 5 while being pulled in through the through hole 13. The used needle of the needle-and-hub body is wound two or three turns about the needle winding axle 5 by rotating the cylindrical container 6 two or three times as seen from FIGS. 6 and 7. Finally the tip of the used needle is pulled in the cylindrical container 6, and once the used needle has been pulled therein, it cannot come up from the cylindrical container 6 again unless the cylindrical container 6 is broken, thus assuring that nobody can be injured by the used needle.

If the needle 3 is thick enough to cause counter action to the winding operation of the cylindrical container 6, and if the right hand is put apart from the cylindrical container 6 after every turn, the cylindrical container may be rotated in the unwinding direction, allowing the used needle to protrude from the ceiling of the cylindrical container 6 again.

The detent means, however, prevents the unwinding of the used needle once it has been wound about the needle winding axle 5.

Figure 9:
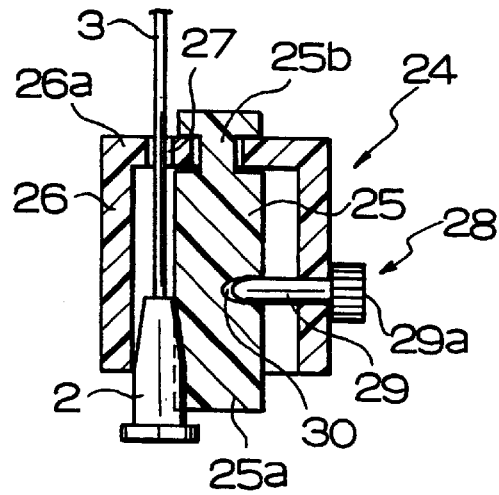
FIG. 9 is an enlarged longitudinal section of the disposable container of a safety injector according to a second embodiment.

Referring to FIG. 9, a safety injector according to the second embodiment of the present invention is so designed as to be appropriate for use in winding a needle of relatively thinness. Specifically, the needle winding-and-storing means 24 comprises a winding axle 25 fixed to the hub 2 of a needle-and-hub body and a rotary cylindrical container 26 rotatably fixed to the winding axle 25. The lower portion 25a of the winding axle 25 is fixed to the hub 2 of the needle-and-hub body by using adhesive agent.

The center protrusion 25b of the winding axle 25 passes through the ceiling plate 26a of the cylindrical container 26, and the top of the center protrusion 25b appearing from the ceiling plate 26a is joined by flattening to be caught by the ceiling plate 26a, thereby permitting the ceiling plate 26a to rotatably support the winding axle 25. Such joining can be performed by using heating means, ultrasonic means or high-frequency means.

The cylindrical container 26 has a small through hole 27 made in its ceiling plate 26a, and the cylindrical container 26 opens on its bottom side although the bottomless cylindrical container 26 is liable to rattle more or less around the winding axle 25. Such rattle, however, causes no significant influence in winding operation.

In order to suppress such rattle prior to the winding operation rattle-proof means 28 is provided between the needle winding axle 25 and the cylindrical container 26. This rattle-proof means 28 has the effect of preventing any deformation of needle, which, otherwise, would be caused by undesired rotation of the winding axle.

The rattle-proof means 28 is provided for example, in the form of stopper pin 29, which passes through a small through hole in the cylindrical container 26 until its tip has been put in a recess 30, which is made in the winding axle 25, thereby preventing the rattling of the cylindrical container 26 around the winding axle 25, and at the same time, undesired rotation of the winding axle 25.

The stopper pin 29 must be kept thrust into the recess 30 of the winding axle 25 after the injector is used, and before the cylindrical container 26 is rotated. Therefore, the rattle or rotation of the cylindrical container 26 cannot be caused while the injector is being used. The resultant stable condition assures that no dangerous handling is caused.

Just before pulling in and winding the needle of the needle-and-hub body the stopper pin 29 is held by the head 29a with fingers to be pulled out, thereby disengaging the cylindrical container 26 from the winding axle 25 to permit the cylindrical container 26 to rotate in winding direction. Thus, the needle of the needle-and-hub body can be pulled in and wound around the winding axle 25, not permitting the needle of the needle-and-hub body to protrude again from the ceiling of the cylindrical container 26.

Figure 10:
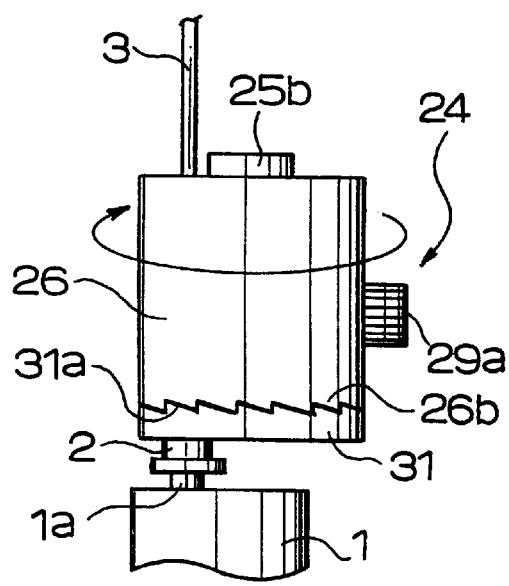
FIG. 10 illustrates the disposable container of a safety injector according to a third embodiment of the present invention.
Figure 11:
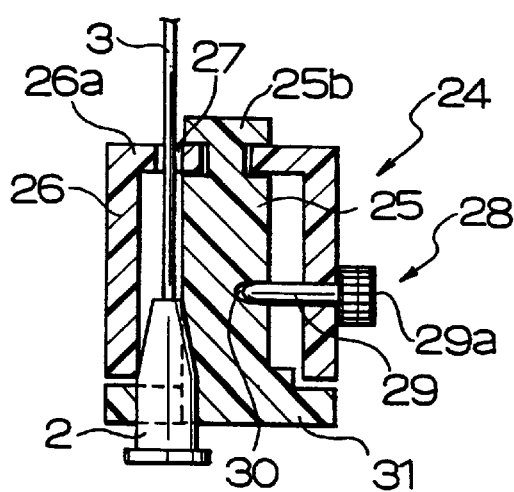
FIG. 11 is a longitudinal section of the container of the safety injector according to the third embodiment.

FIGS. 10 and 11 show a safety injector according to the third embodiment of the present invention. It is different from the second embodiment only in that it has detent means for preventing the cylindrical container from rotating in the opposite or unwinding direction. Parts other than the detent means are same as in the second embodiment, and are indicated by same reference numerals as in FIG. 9 to omit descriptions of such similar parts.

As seen from FIGS. 10 and 11, thewinding axle 25 has a circular flange 31 integrally connected to its bottom, and the circular flange 31 is put in contact with the annular bottom circumference of the cylindrical container 26. The circular flange 31 has sawtooth-like indentations 31a formed on its circumference whereas the annular bottom circumference of the cylindrical container 26 has sawtooth-like indentations 26b formed thereon. Thus, the cylindrical container 26 is permitted to turn only in the winding direction as indicated by arrow in FIG. 10.

The safety injector according to the third embodiment works in the same way as the second embodiment. Thanks to the detent means the cylindrical container 26 can be rotated stable, and thanks to the rattle-proof means 28 the injector can be used with increased safety.

The needle 3 of the needle-and-hub body can be a thin needle, soft needle or resin needle of all or partial resin, thereby facilitating the winding of the needle 3 of the needle-and-hub body.

What is claimed is:

1. A device for winding and storing a used needle of an injector, the device being mountable to a tip end of a syringe of the injector and comprising:
    a needle-hub assembly having a hub;
    a cylindrical container having a bottom wall;
    a needle winding axle rotatably fixed within said cylindrical container to permit said cylindrical container to turn about said needle winding axle; and
    detent means for preventing said cylindrical container from turning in an unwinding direction, wherein the hub of said needle-hub assembly is fixed to the bottom wall of said cylindrical container therethrough at an eccentric position relative to a longitudinal axis thereto.

2. The device according to claim 1 further comprising: rattle-proof means for preventing any adverse action prior to the needle winding operation, said rattle-proof means provided between said needle winding axle and said cylindrical container.

3. The device according to claim 2 wherein said rattle proof means comprises a stopper pin insertable through a hole formed in a cylindrical wall of said cylindrical container, said stopper pin having a tip end that extends into a recess formed in said winding axle.

4. The device according to claim 1 further comprising a thumb catch integrally connected to either one of the hub of said needle-hub assembly and the said needle winding axle to assist the needle winding operation.

5. The device according to claim 1, wherein said detent means comprises sawtooth indentations formed on an annular bottom of said cylindrical container and a resilient ramp piece that is detachably engagable with the sawtooth indentations.

6. The device according to claim 1, wherein said detent means comprises sawtooth indentations formed both on an annular bottom of said cylindrical container and a plateau flange defining a narrow gap therebetween.

* * * * *